(12) United States Patent
Kralik (10) Patent No.: US 11,992,567 B2
(45) Date of Patent: May 28, 2024

(54) BRISTLE RING DIFFUSER

(71) Applicant: Western Technology, Inc., Bremerton, WA (US)

(72) Inventor: Michael S. Kralik, Draper, UT (US)

(73) Assignee: Western Technology, Inc., Bremerton, WA (US)

( * ) Notice: Subject to any disclaimer, the term of this patent is extended or adjusted under 35 U.S.C. 154(b) by 381 days.

(21) Appl. No.: 17/520,951

(22) Filed: Nov. 8, 2021

(65) Prior Publication Data

US 2022/0143238 A1     May 12, 2022

Related U.S. Application Data (60) Provisional application No. 63/110,858, filed on Nov. 6, 2020.

(51) Int. Cl.
| | |
|---|---|
| *A61L 2/10* | (2006.01) |
| *A46B 9/02* | (2006.01) |
| *A46B 17/06* | (2006.01) |
| *A61L 2/26* | (2006.01) |

(52) U.S. Cl.
CPC ............... *A61L 2/10* (2013.01); *A46B 9/025* (2013.01); *A46B 17/065* (2013.01); *A61L 2/26* (2013.01); *A61L 2202/11* (2013.01)

(58) Field of Classification Search
CPC .......... A61L 2/10; A61L 2/26; A61L 2202/11; A46B 9/025; A46B 17/065
See application file for complete search history.

(56) References Cited

U.S. PATENT DOCUMENTS

| | | |
|---|---|---|
| 6,239,442 B1 | 5/2001 | Limura |
| 6,343,400 B1 | 2/2002 | Massholder et al. |
| 6,902,397 B2 | 6/2005 | Farrell et al. |
| 7,444,711 B2 | 11/2008 | Garcia et al. |
| 8,105,532 B2 | 1/2012 | Harmon et al. |
| 9,265,850 B2 | 2/2016 | Davis et al. |
| 2005/0166863 A1 | 8/2005 | Park et al. |
| 2006/0185116 A1 | 8/2006 | Lee et al. |
| 2008/0253941 A1 | 10/2008 | Wichers et al. |
| 2022/0079414 A1* | 3/2022 | Desu-Kalyanam ..... A47L 23/02 |

FOREIGN PATENT DOCUMENTS

| | | |
|---|---|---|
| KR | 100864187 B1 | 10/2005 |
| WO | WO 02/21970 A1 | 3/2022 |

OTHER PUBLICATIONS

Saalmann, "Saalux UV-comb", www.saalmann-medical.de/uv/phototherapy/saalux-uv-comb/?L=1, accessed May 18, 2020.

\* cited by examiner

*Primary Examiner* — Nicole M Ippolito
(74) *Attorney, Agent, or Firm* — Thorpe North & Western, LLP.

(57) ABSTRACT

A bristle ring diffuser for diffusing UV light is described herein. In one example, the radiation diffuser cone comprises a base and a plurality of bristles. The base has an interface which is coupleable to an object having an ultraviolet (UV) light source. The base also has an aperture which aligns with the UV light source when the interface is coupled to the UV light source. The plurality of bristles is arranged about the aperture and extend from the base. The plurality of bristles is opaque to UV light and is angled away from a central axis of the aperture.

24 Claims, 8 Drawing Sheets

BRISTLE RING DIFFUSER

RELATED APPLICATION

This application claims priority to U.S. Provisional Application No. 63/110,858, filed Nov. 6, 2020 which is incorporated herein by reference.

BACKGROUND

Short-wavelength ultraviolet (UV) light is commonly used to sterilize surfaces and generally spans about 100 nanometers to about 400 nm. Wavelengths in the UVC range between about 100 nm and 280 nm are strongly absorbed by nucleic acids, which can result in the death or inactivation of microorganisms. The effectiveness of the UV sterilization is dependent upon the intensity of the radiation, the wavelength, and the length of time the microorganism is exposed to the UV light (e.g. dosage). Additionally, the UV light should be concentrated on the microorganism, since stray UV light may harm other surfaces.

SUMMARY

The subject matter disclosed herein can improve the utility and safety of a UV light source in disinfecting surfaces. Additionally, some examples of the disclosed subject matter can inhibit stray UV light from harming other surfaces while also acting to dislodge debris and maintain a desired distance from a surface.

Various exemplary embodiments of a bristle ring diffuser are described herein. In one embodiment, a radiation diffuser cone comprises a base and a plurality of bristles extending from the base. The base has an interface which is coupleable to an object having an ultraviolet (UV) light source. The base also includes an aperture which aligns with the UV light source when the interface is coupled to the UV light source. The plurality of bristles can be arranged about the aperture and extend from the base. The plurality of bristles can also be opaque to UV light and can be angled away from a central axis of the aperture.

In another embodiment, a system for disinfecting a surface is provided. The system can include an object having a UV light source and a bristle ring cone diffuser. The bristle ring cone diffuser can comprise a base coupled to the object having a UV light source and an aperture aligned with the UV light source, and a plurality of bristles arranged about the aperture and extending from the base, the plurality of bristles being opaque to UV light and being angled away from a central axis of the aperture.

There has thus been outlined, rather broadly, features of the disclosed technology so that the detailed description thereof that follows may be better understood, and so that the present contribution to the art may be better appreciated. Other features will become clearer from the following detailed description, taken with the accompanying drawings and claims, or may be learned by the practice of the disclosed technology.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the disclosed technology, it should be understood that other embodiments may be realized and that various changes may be made without departing from the spirit and scope of the present invention. Thus, the following more detailed description of the disclosed technology is not intended to limit the scope of the invention, as claimed, but is presented for purposes of illustration only and not limitation to describe the features and characteristics of the disclosed technology and to sufficiently enable one skilled in the art to practice the disclosed technology. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a pivot" includes reference to one or more of such features and reference to "pressing" refers to one or more such steps.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 2%, and most often less than 1%, and in some cases less than 0.01%.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Figure 1:
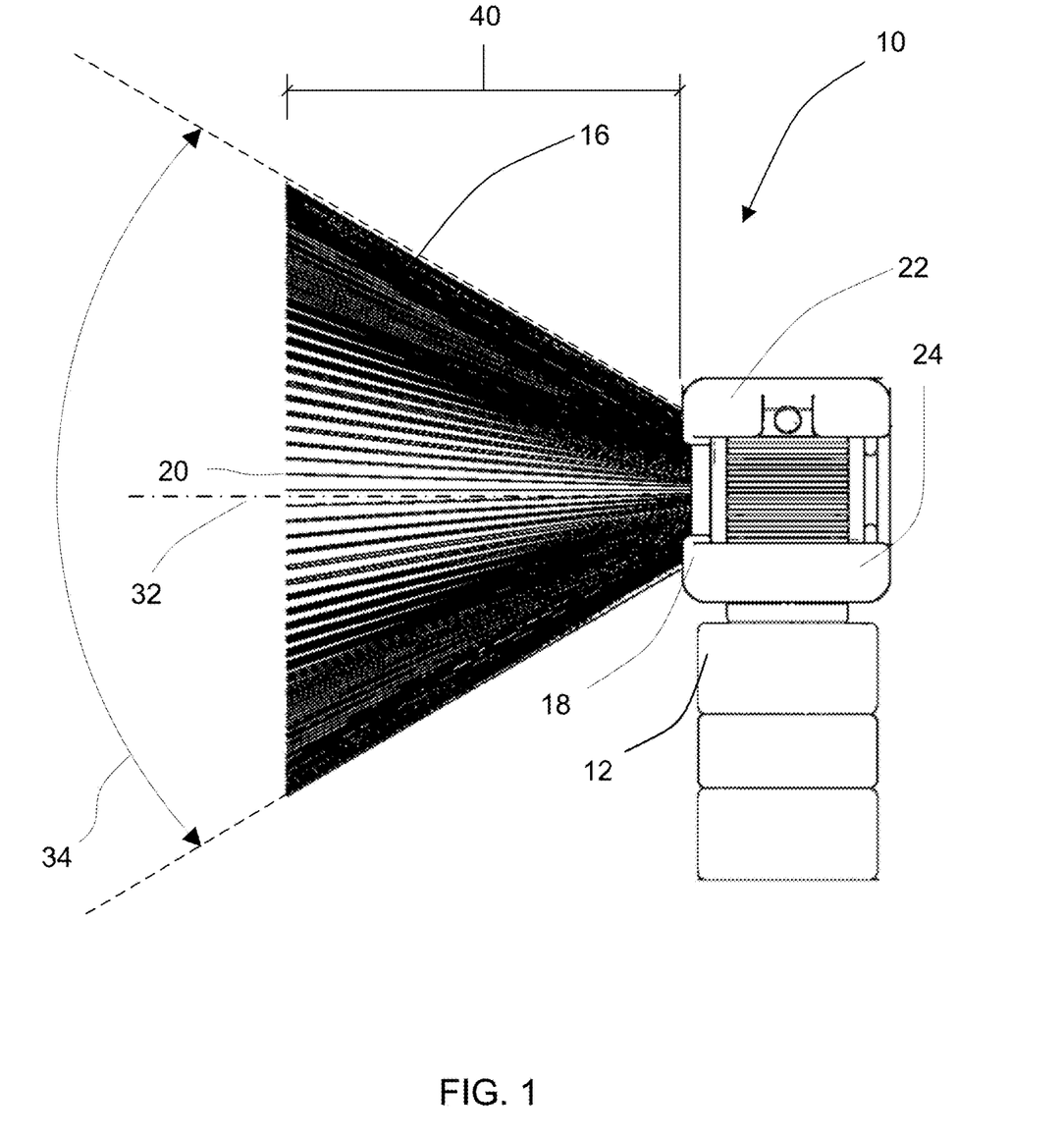
FIG. 1 illustrates a side view of an example of a system for disinfecting a surface including a bristle ring diffuser mounted to a UV light source in accordance with one example.
Figure 2:
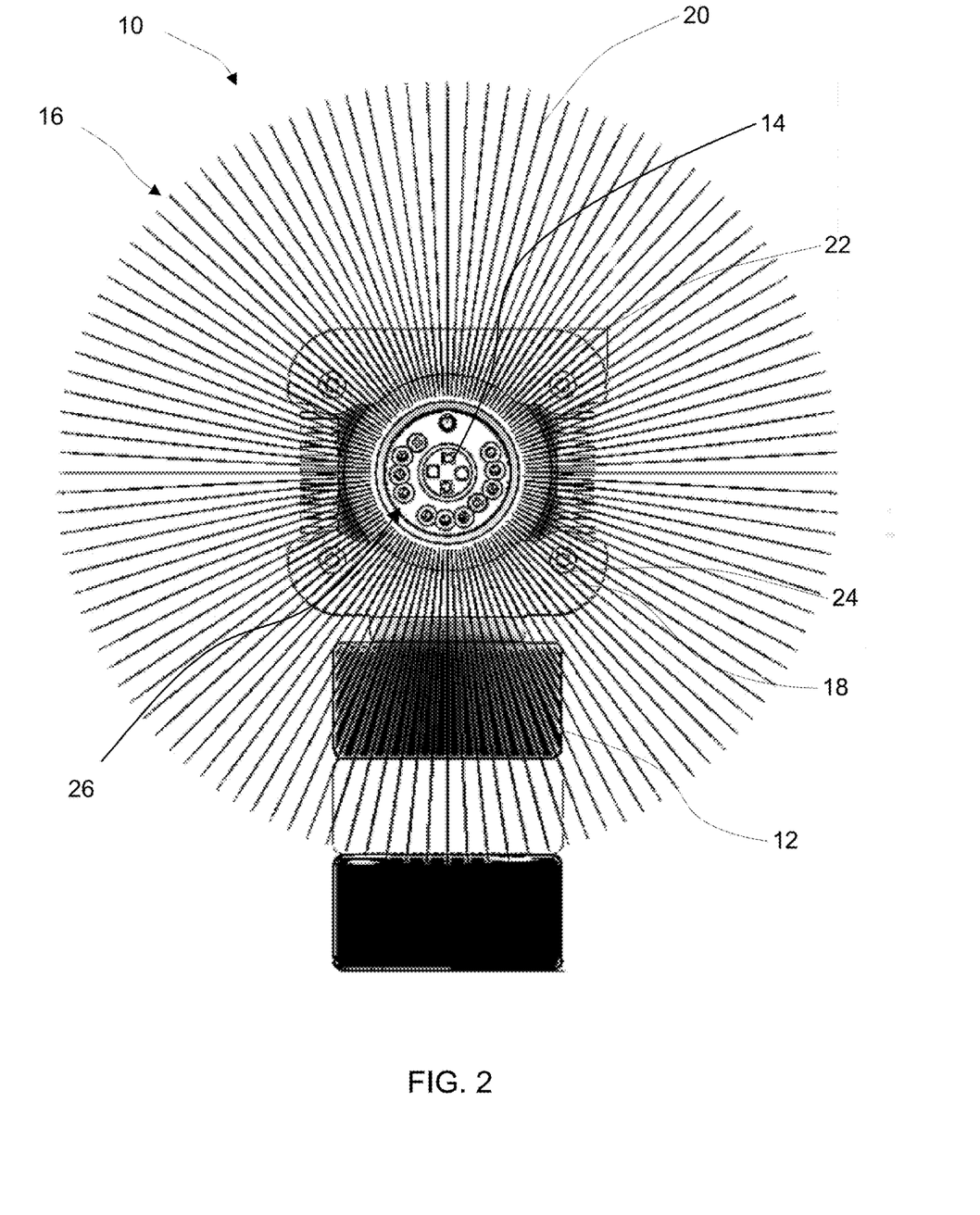
FIG. 2 illustrates a front view of the system for disinfecting a surface of FIG. 1.

FIGS. 1 and 2 depict an example of a system 10 for disinfecting a surface. The system comprises an object 12 having a UV light source 14 and a bristle ring diffuser 16. The bristle ring diffuser 16 is coupled to the UV light source 14 and acts as a curtain around a cone of UV light projected by the UV light source 14. The object 12 can be any object that houses a UV light source. For example, the object 12 can be a battery-powered handheld object with a UV light source, or it could be a hardwired object having a UV light source. The UV light source 14 can be any UV light source that is operable to project UV light from the object 12. For example, the UV light source 14 can be a mercury-vapor lamp, a light emitting diode, or other type of UV lamp. In one example, the UV light source is a UVC light source. In another example, the UVC light source can emit UV light having a wavelength of 100 nm to 280 nm.

The bristle ring diffuser 16 comprises a base 18 and a plurality of bristles 20. The base 18 has an interface which is coupleable to the object 12 having the UV light source 14.

In the example of FIGS. 1 and 2, the base 18 comprises a ring in which the plurality of bristles are fixed. The base can then be secured to corresponding attachment features on the object 12. For example, a clam shell design that has a first portion 22 and a second portion 24 which sandwich a portion of the object 12 can include attachment features which mate with the base, thereby coupling the base 18 to the object 12. The base 18 has an aperture 26 that aligns with the UV light source 14 when the base 18 is coupled to the object 12. Thus, the UV light source 14 projects UV light through the aperture 26 when the base 18 is coupled to the object 12. Alternatively, the base can be a plurality of arc segments which have corresponding attachment features on the object.

The plurality of bristles 20 can be arranged about the aperture 26 and extend away from the base 18. For example, if the aperture 26 is a circle as shown in FIGS. 1 and 2, the plurality of bristles 20 can be arranged as a circle around the aperture 26. The aperture can alternatively be an oval, square, rectangle or other suitable shape. In one alternative, all or at least a portion of the bristles can be light pipes that directly focus the emitted radiation. In this case, these bristles can be oriented having one proximal end oriented in front of the light source so that light is directed along the bristles and out the opposing distal end. For example, a portion of bristles can be light pipes which are oriented around a periphery of the light source but still in front of the light source. In another alternative, light pipe bristles can be arranged to substantially completely cover the light source such that substantially all of the emitted radiation is collected and directed through the light pipes. In still another alternative, light pipe bristles having an external side face directed toward the emission source can collect misdirected radiation emission.

Figure 3A:
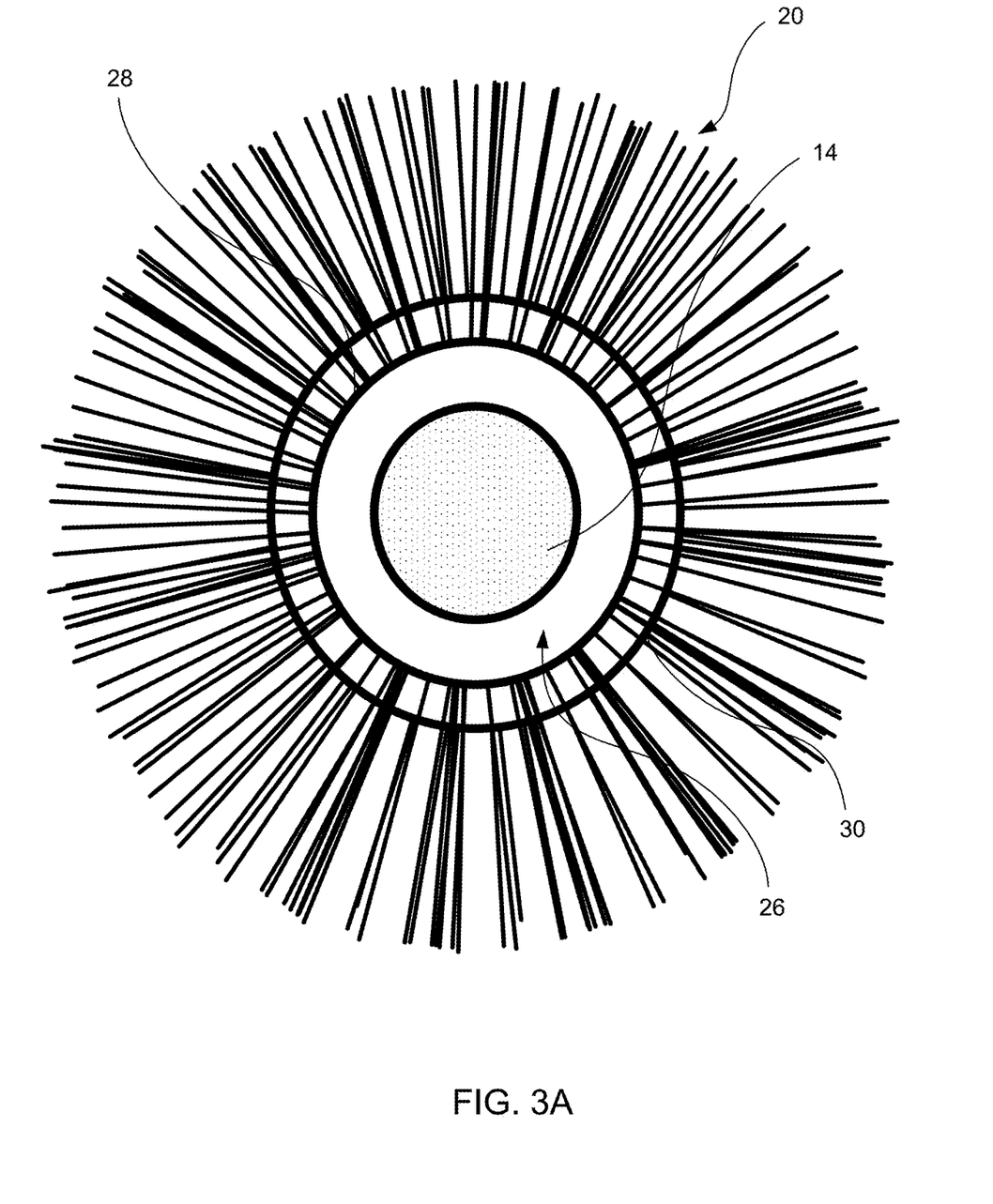
FIG. 3A illustrates an example profile of a multi-layered bristle arrangement of a bristle ring diffuser in accordance with another example.

In some examples, such as the example shown in FIG. 3A, the plurality of bristles 20 can be arranged in rows, such as a first and second concentric row 28, 30 around the aperture 26. Together, the plurality of bristles 20 can form an opaque curtain about the aperture 26. In some examples, bristles of the plurality of bristles 20 can overlap to form an opaque curtain. More specifically, the overlap can be an overlap as viewed from a side of the bristle cone such that UV light does not emit beyond the cone. This may be accomplished by choosing bristle diameters and offsetting each row so as to achieve sufficient blocking of UV light outside of the cone. Alternatively, or in addition, clusters of bristles can be oriented around the perimeter of the aperture. For example, bristle diameters can range from about 0.01 mm to about 2 mm, and often from about 0.05 mm to 1 mm.

Regardless, each bristle of the plurality of bristles 20 may be individually opaque to UV light, or in some examples, while each individual bristle may not be opaque, the overall plurality of bristles 20 may be opaque. More specifically, a single bristle may be translucent to block only a portion of UV light while additional bristles may cumulatively block substantially all the UV light so as to be opaque in combination. The bristles may be formed of a material that is naturally opaque to UV light, or they may be coated in a material that is opaque to UV light. In another example, the UV bristles may be reflective on all or a portion of a bristle. Thus, a bristle surface on an interior of the bristle ring diffuser 16 may reflect light back towards the inner volume of the cone.

As shown in FIG. 1, the plurality of bristles can form a frustoconical shape that is open at both ends. A central axis 32 of the frustoconical shape can be aligned with a central axis of a radiation pattern of the UV light source 14. The UV light source 14 can project a conical pattern having a conical apex angle 34 and the plurality of bristles can be angled to have a conical apex angle that matches the conical apex angle of the UV light source. The perimeter cone pattern of bristles can be arranged in density and pattern in order to prevent a line of sight to the UV light source outside of the conical light projection space defined by the bristle cone.

A length 40 of the bristle ring diffuser 16 can be selected to ensure a predetermined minimum exposure of UV light is applied at distal end of the plurality of bristles 20. Thus, the bristle ring diffuser 16 can be helpful in guiding a user to maintain a desired distance from a surface being disinfected by brushing the surface with the bristle ring diffuser 20. The length can be selected based on the intensity of the UV light source 14 and the speed at which the UV light will be swept over the surface. A desired dose of UV light typically falls between 2,000-8,000 micro watt seconds per square centimeter. In order to assist in measuring dosage, the bristle ring diffuser and/or light source can include a timer, a motion sensor, or other dosimeter to estimate UV dosage. For example, the bristles can include an indicator scale down the length of the bristle (e.g. numbers, colors, texture, shape, etc.) to facilitate a relative measure of dosage timing for inactivation of a microorganism. For instance, the bristles could have five different sections of color with red at the end of the bristle indicating, as an example, a 5 second viral kill, up to green at the top, nearest the emission source, indicating a 1 second kill time. When the light is moved closer to the surface, the bristles flare or move tangentially to the surface allowing the bristle scale to indicate a faster germicidal action.

The plurality of bristles can be selected to have a stiffness sufficient to dislodge particulate matter on the surface to be disinfected. UV disinfection requires a line of sight between the UV light source and the microorganisms. If the line of sight is disrupted by a small object such as dust, the UV disinfection may be ineffective. Thus, the bristles can be sufficiently stiff to dislodge such objects.

Figure 3B:
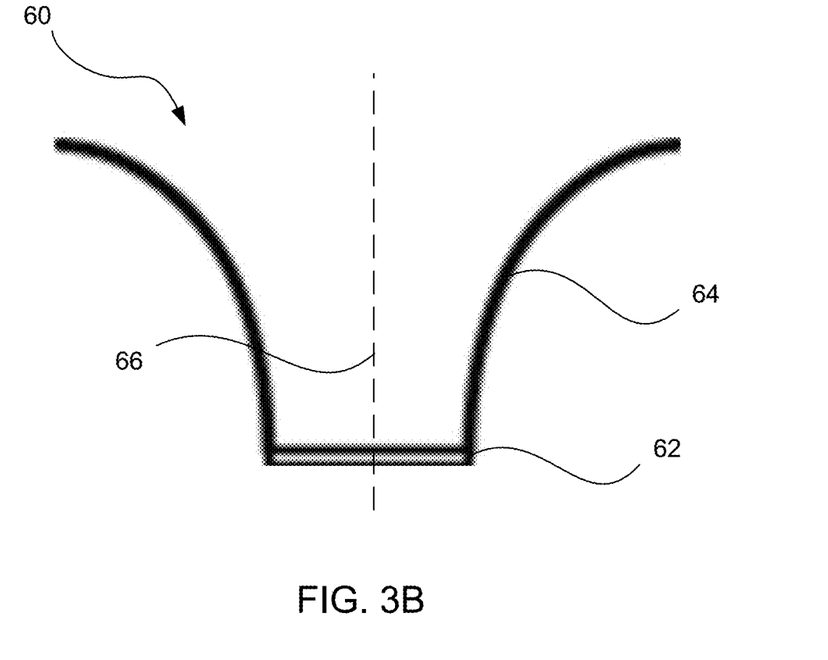
FIG. 3B illustrates an example side profile having outwardly curved bristles in accordance with another example.
Figure 3C:
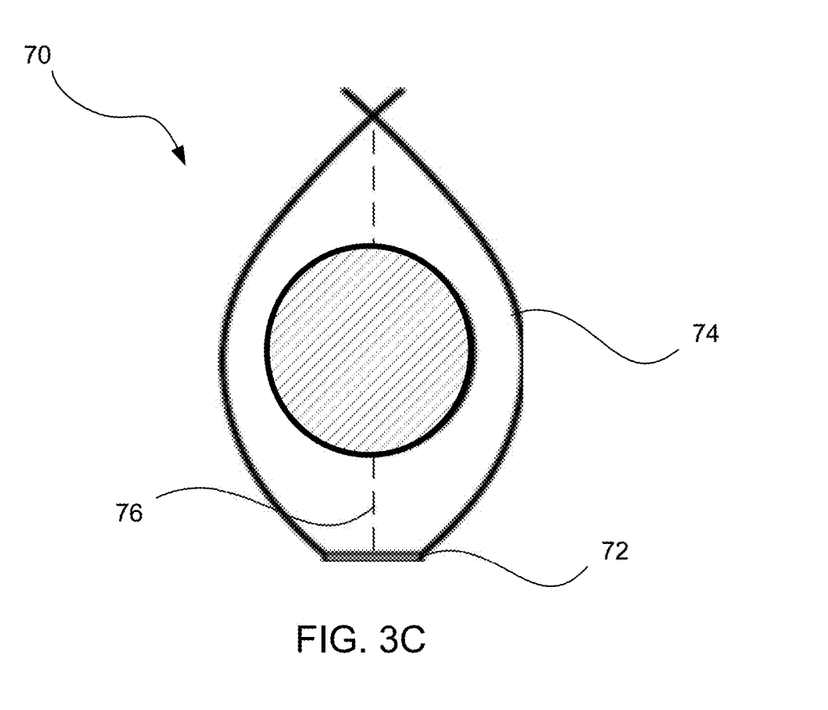
FIG. 3C illustrates an example side profile having curved bristles to form an enclosed space in accordance with another example.

The curvature and shape of the bristles can also be varied to achieve specific results. For example, bristles can be outwardly curved in order to reduce stray light emission when contacting a surface. FIG. 3B shows a bristle ring diffuser 60 having a base 62 with bristles 64 that curve outwardly from a central aperture axis 66. This outward curvature can help to prevent bristles from bending inward while moving across a surface. This can avoid undesirable blocking of the emitted radiation from reaching the surface. Further, the degree of overlap and bristle density can be adjusted so as to prevent undesirable radiation leakage outside the bristle cone during use. In another example, FIG. 3C illustrates a bristle ring diffuser 70 with bristles 74 which that curve outwardly from a central axis 76 near a base 72 and then curve back inwardly toward a distal end. In this manner, the curvature forms an enclosed space which can envelope an object to be treated. For example, a handrail, pipe, doorknobs, tools, handles, etc. can be entirely or partially enveloped by this teardrop shaped enclosed space so as to prevent or reduce emitted radiation from reaching beyond the enclosed space so as to limit radiation contact distance.

FIG. 4A-4E illustrates various cross sections of bristles of the plurality of bristles 16 and several arrangements. Cross section 36 is a curved cross section with an apex 38 pointing away from the central axis 32 of the aperture 26. For example, in FIG. 4A the central axis 32 of the aperture 26 would be below the cross section 36. In some examples, the inner curve facing the central axis 32 of the aperture 26 can be reflective to reflect UV light back towards the central axis 32. Cross section 40 is an example of a rectangular cross section of a bristle. Other shapes are possible such as circular cross sections, square cross sections, oval cross sections, triangular, parabolic, and star shape cross sections. Further, the bristles can be specifically shaped to include reflective faces/curvatures which facilitate scattered radiation to be re-directed back to the surface.

Figure 4A:
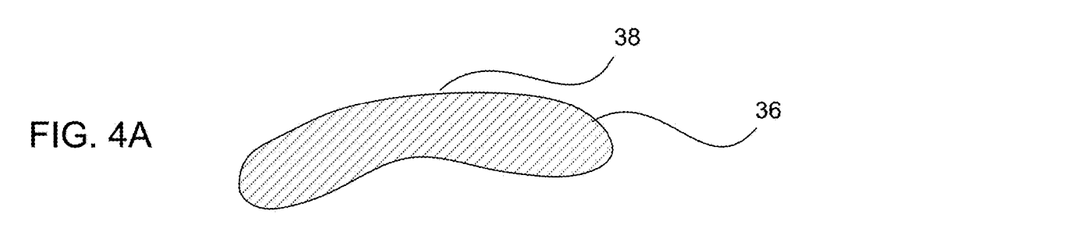
FIG. 4A-4F illustrate several bristle cross-sections and bristle patterns in accordance with multiple examples.
Figure 4B:
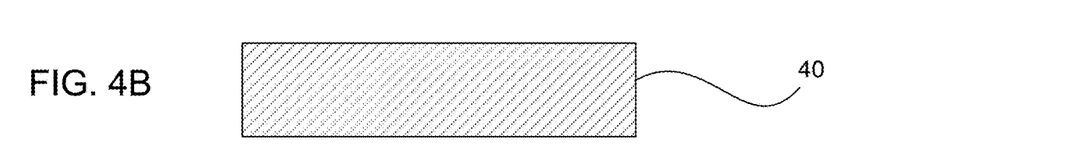
Figure 4C:
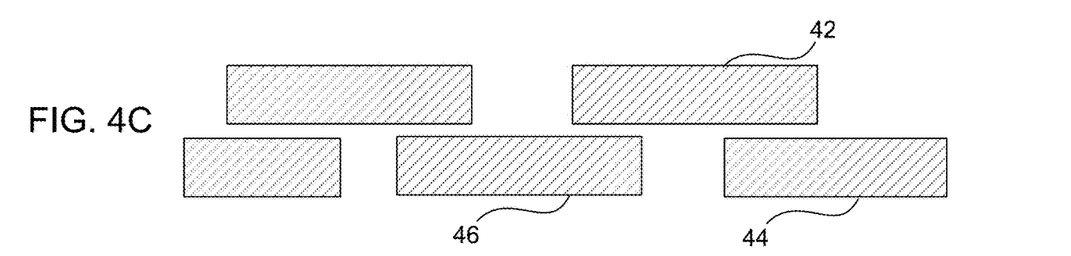
Figure 4D:
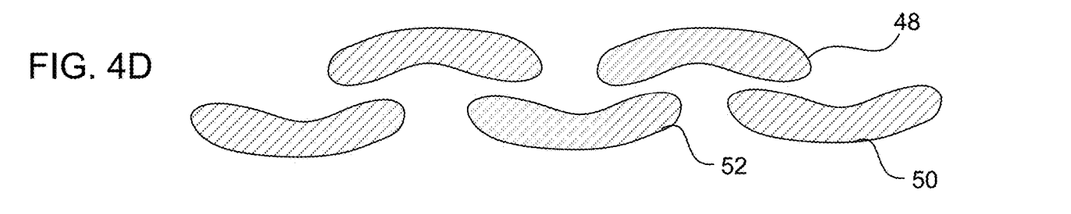
Figure 4E:
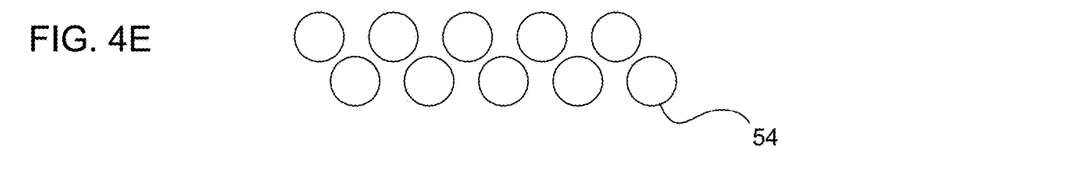
Figure 4F:
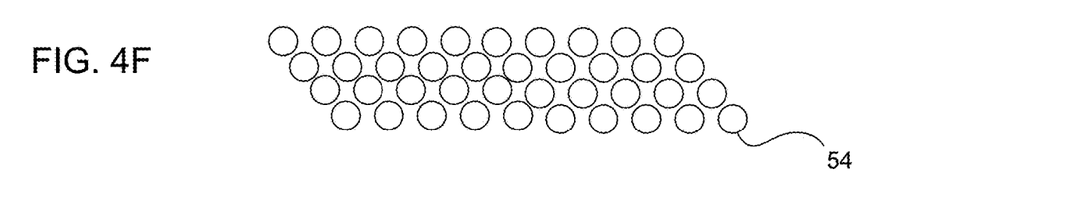

As shown in FIG. 4C-4F, the cross sections of the bristles may overlap. For example, cross section 42 overlaps with cross sections 44 and 46. The overlapping layers of bristles can better inhibit the passage of UV light compared to a single layer. As illustrated in FIG. 4D, cross sections 48, 50, and 52 are examples of overlapping bristles having curved cross sections. FIG. 4E illustrates circular cross-section bristles 54 which overlap and are offset. FIG. 4F shows a multi-layered pattern in which the bristles are more than two deep, i.e. in this case four deep, although the pattern can include any number of bristles such as four to twenty deep. In one example, a composite mixture of bristle shapes can be used. For example, a portion of the bristles can have a flattened rectangular cross-section, while a second portion can have a circular cross-section which can be randomly or evenly mixed. In another alternative, the bristles can be anti-static and listed as 94V-0 for flame retardance.

Figure 5:
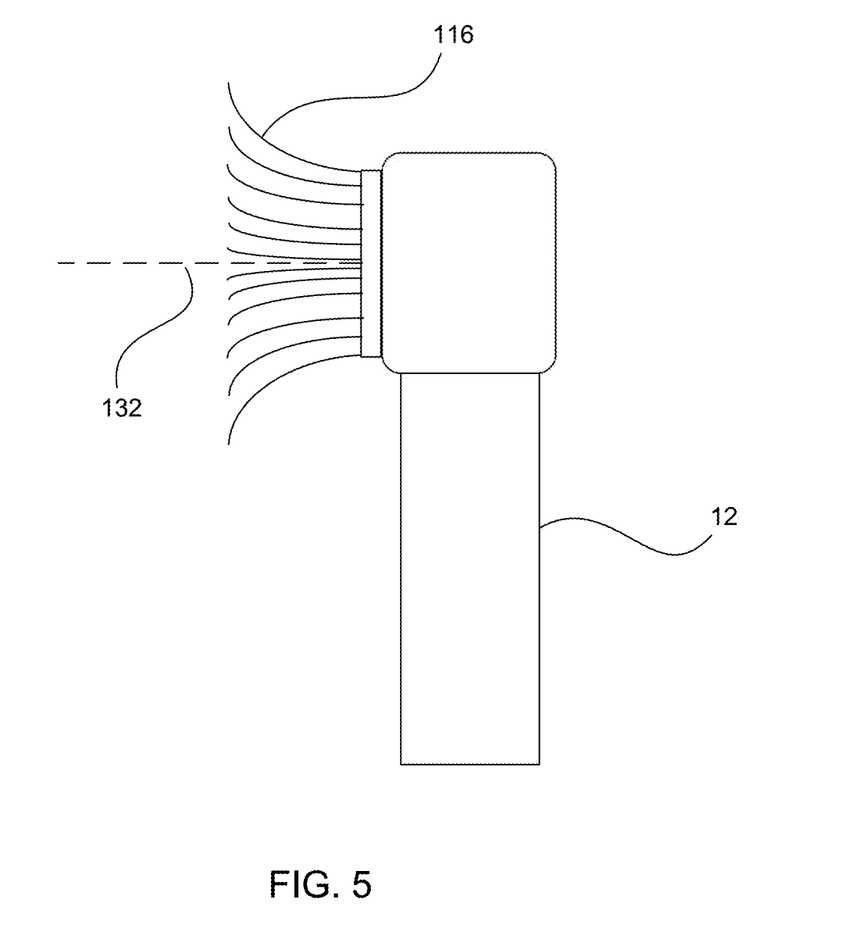
FIG. 5 illustrates another example of a bristle ring diffuser having outwardly curved bristles and coupleable to an object having a UV light source in accordance with one example.

FIG. 5 illustrates an example of an object 12 with a UV light source having an outwardly curved bristle ring diffuser 116. At least one bristle of the bristle ring diffuser 116 can curve outward, away from a central axis 132 of the bristle ring diffuser 116. Thus, the bristle ring diffuser 116 can have a curved frustoconical shape.

Figure 6:
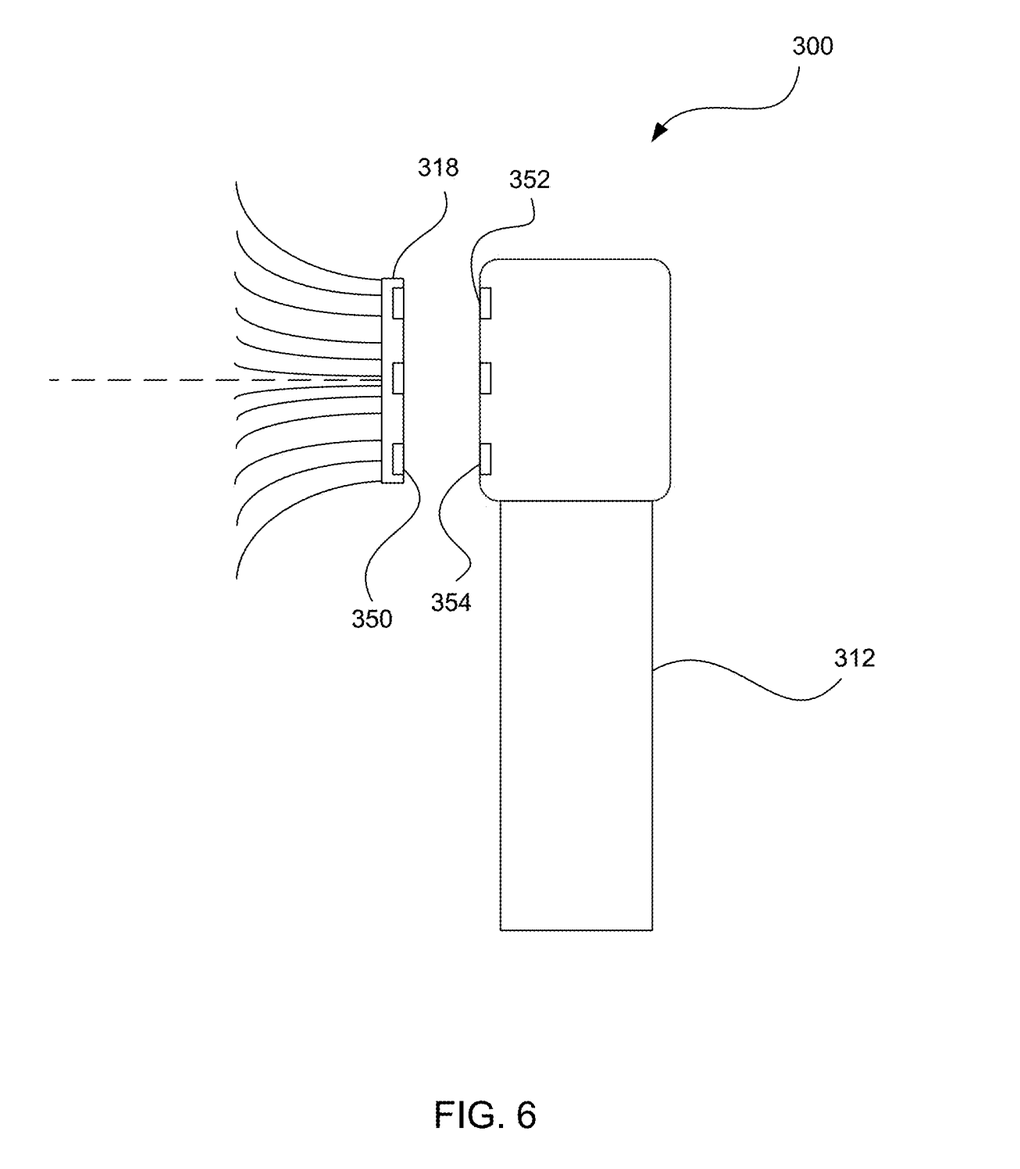
FIG. 6 illustrates a magnetic coupling between a bristle ring diffuser and a UV light source in accordance with one example.

FIG. 6 illustrates an example of a system 300 for disinfecting a surface with a magnetic attachment coupling. The system 300 is similar to the system of FIGS. 1 and 2 with the exception of the base 318. The base 318 is coupleable to the object 312 by way of magnets 350. The object 312 can have complementary magnets 352 or magnetizable materials, or in some instances the object may have a face 354 comprising a magnetic or magnetizable material. Thus, the complementary sides can have permanent magnets which are oriented with opposing magnetic poles, or one side can include a permanent magnet while the complementary feature on an opposite surface can be a magnetizable material (e.g. ferromagnetic material). Thus, the bristle ring diffuser 316 can be coupled to the object through the magnetic attraction of magnets 350 and 352 or between the magnets 350 and the face 354 of the object, or complimentary magnetizable elements.

Figure 7:
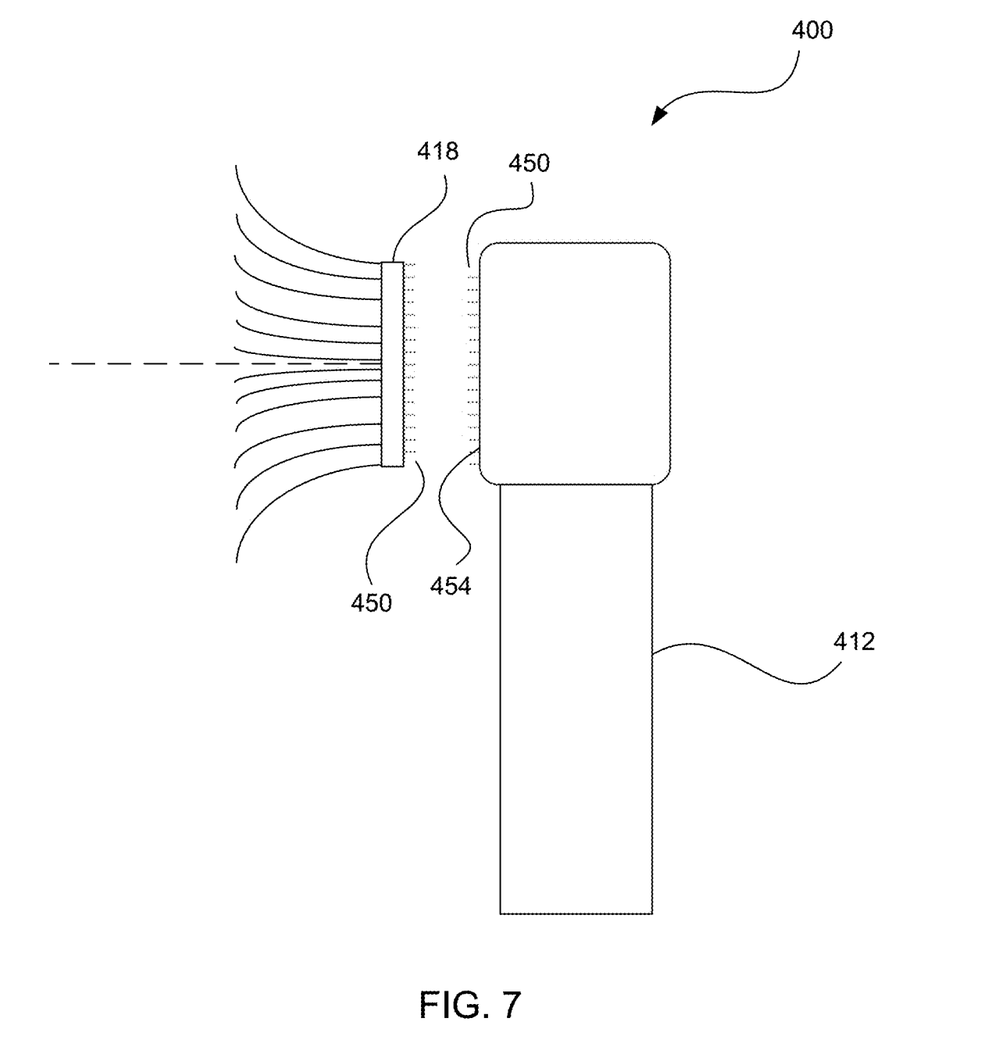
FIG. 7 illustrates an example of a hook and loop fastener coupling between a bristle ring diffuser and a UV light source in accordance with yet another example.

FIG. 7 illustrates another example of a system 400 for disinfecting a surface. The system 400 is similar to the system of FIGS. 1 and 2 with the execution of the base 418. The base 418 can be coupleable to the object 412 by way of hook and loop fasteners 450. The base 418 may be coupled to the object 412 by pressing the base 418 against the face 454 of the object 412 thereby securing the hook and loop fasteners.

Other attachment mechanisms can include, but are not limited to, groove and pin, detents, threaded engagement surfaces, retractable coupler ring mechanisms, push-pin spring couplers, magnetic couplings, and the like.

In some cases the UV light source can emit light across a band of undesirable wavelengths based on a particular surface. For example, xenon flash lamps emit radiation across visible and UV wavelengths, including UVA and UVB. UVA and UVB may be damaging to a particular surface, while visible wavelengths may cause a photosensitive reaction (e.g. when using in a dark room). In order to eliminate such undesirable wavelengths from a broadband light source, a band-pass filter can be coupled to the base to span the aperture. Suitable band-pass filters may allow only UVC light (e.g. around 265 nm), although other band-pass filters can be selected based on the desired wavelengths. Accordingly the diffuser can facilitate controlled absorption of any wavelengths of light such that other light sources may be used (e.g. infrared, visible, etc).

In another example, a kit for modifying an object having a UV light source is described. For example, modifying object 12 to use the bristle ring diffuser 16 can include mounting an attachment feature onto a housing of the object. The kit can include any of the previously described bristle ring diffusers and instructions describing how to attach the base of a bristle ring diffuser to the object. For example, mounting the attachment feature can include adhesive, drilling into the housing, clamps, or the like.

As shown above, the described system for disinfecting a surface and the bristle ring diffuser can be used to disinfect a surface while minimizing unwanted stray radiation on nearby surfaces. Additionally, the bristle ring diffuser may dislodge particulate on the surface enhancing the disinfection by the UV light. The bristle ring diffuser may be used with most sources of UV light for disinfection.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A bristle ring diffuser, comprising:
    a base comprising:
        an interface which is coupleable to an object having an ultraviolet (UV) light source, and
        an aperture which aligns with the UV light source when the interface is coupled to the UV light source; and
    a plurality of bristles arranged about the aperture and extending from the base, the plurality of bristles being opaque to UV light and being angled away from a central axis of the aperture.

2. The bristle ring diffuser of claim 1, wherein the bristles of the plurality of bristles overlap to form an opaque curtain.

3. The bristle ring diffuser of claim 1, wherein each bristle of the plurality of bristles is reflective to UV light.

4. The bristle ring diffuser of claim 1, wherein the plurality of bristles form a frustoconical shape.

5. The bristle ring diffuser of claim 1, wherein each bristle of the plurality of bristles has a rectangular cross-section.

6. The bristle ring diffuser of claim 1, wherein each bristle of the plurality of bristles has a curved cross section with an apex of the curved cross section pointing away from the central axis of the aperture.

7. The bristle ring diffuser of claim 1, wherein each bristle of the plurality of bristles curves away from the central axis of the aperture.

8. The bristle ring diffuser of claim 1, wherein the plurality of bristles has a length selected to ensure a predetermined minimum exposure to the UV light source at a distal end of the plurality of bristles.

9. The bristle ring diffuser of claim 8, wherein the predetermined minimum exposure is a dosage of UV light sufficient to disinfect a surface.

10. The bristle ring diffuser of claim 1, wherein each of the bristles of the plurality of bristles has a stiffness selected to dislodge particulate matter on a surface.

11. The bristle ring diffuser of claim 1, wherein the bristles of the plurality of bristles are arranged in a plurality of overlapping rows of bristles.

12. The bristle ring diffuser of claim 1, wherein at least a portion of the plurality of bristles include a dosage indicator scale along a length of the respective bristles.

13. The bristle ring diffuser of claim 1, wherein at least a portion of the plurality of bristles are light pipes with a proximal end oriented to collect at least a portion of the UV light.

14. The bristle ring diffuser of claim 1, wherein at least a portion of the plurality of bristles have an outwardly curved profile from a central aperture axis.

15. The bristle ring diffuser of claim 1, wherein the UV light source has a conical apex angle and the plurality of bristles are angled to match the conical apex angle.

16. The bristle ring diffuser of claim 1, further comprising a band-pass filter attached to the base and oriented to span the aperture.

17. A kit for modifying an object having an ultraviolet (UV) light source, the kit comprising:
    a bristle ring diffuser comprising:
        a base comprising:
            an interface which is coupleable to the object having the UV light source, and
            an aperture which aligns with the UV light source when the interface is coupled to object; and
        a plurality of bristles arranged about the aperture and extending from the base, the plurality of bristles being opaque to UV light and being angled away from a central axis of the aperture; and
    instruction detailing how to attach the base to the object.

18. A system for disinfecting a surface, comprising:
    an object having a UV light source; and
    a bristle ring diffuser comprising:
        a base coupled to the object having an ultraviolet (UV) light source, the base comprising an aperture aligned with the UV light source; and
        a plurality of bristles arranged about the aperture and extending from the base, the plurality of bristles being opaque to UV light and being angled away from a central axis of the aperture.

19. The system of claim 18, wherein the UV light source projects a conical pattern having a conical apex angle.

20. The system of claim 19, wherein the plurality of bristles is angled to match the conical apex angle.

21. The system of claim 18, wherein the plurality of bristles has a length selected to ensure a predetermined minimum exposure to the UV light source at a distal end of the plurality of bristles.

22. The system of claim 21, wherein the predetermined minimum exposure is a dosage of UV light sufficient to disinfect a surface.

23. The system of claim 21, wherein each bristle of the plurality of bristles has a curved cross section with an apex of the curved cross section pointing away from the central axis of the aperture.

24. The system of claim 21, wherein each bristle of the plurality of bristles are reflective to UV light.

* * * * *